United States Patent [19]

Sanagawa et al.

[11] Patent Number: 5,479,834
[45] Date of Patent: Jan. 2, 1996

[54] APPARATUS HAVING A PIVOTED EDDY CURRENT PROBE FOR DETECTING FLAWS IN THE INNER SURFACE OF A HOLE

[75] Inventors: Toshio Sanagawa; Naoya Shimizu, both of Kobe, Japan

[73] Assignee: Mitsubishi Jukogyo Kabushiki Kaisha, Tokyo, Japan

[21] Appl. No.: 266,156

[22] Filed: Jun. 27, 1994

Related U.S. Application Data

[63] Continuation of Ser. No. 841,097, Feb. 25, 1992, abandoned.

[30] Foreign Application Priority Data

Mar. 6, 1991 [JP] Japan ................................. 3-040027

[51] Int. Cl.⁶ ........................................................ G01D 21/00
[52] U.S. Cl. ............................................. 73/866.5; 324/220
[58] Field of Search ..................................... 324/219, 220, 324/221; 33/502, 503, 559, DIG. 1; 73/865.8, 866.5, 623; 376/245, 249

[56] References Cited

U.S. PATENT DOCUMENTS

| | | | |
|---|---|---|---|
| 3,279,079 | 10/1966 | Schiler | 33/556 |
| 3,718,855 | 2/1973 | Rogel et al. | 324/37 |
| 3,780,571 | 12/1973 | Wiesener | 73/623 |
| 3,823,482 | 7/1974 | Schiler | 33/169 R |
| 3,862,578 | 1/1975 | Schlüter | 73/623 |
| 4,139,822 | 2/1979 | Urich et al. | 324/219 |
| 4,441,078 | 4/1978 | Lecomte | 324/219 |
| 5,025,215 | 6/1991 | Pirl | 73/623 |

FOREIGN PATENT DOCUMENTS

| | | |
|---|---|---|
| 0264687 | 4/1988 | European Pat. Off. . |
| 0411874 | 2/1991 | European Pat. Off. . |
| 1544088 | 9/1967 | France . |
| 2631731 | 11/1989 | France . |
| 3503488 | 7/1986 | Germany ............. 73/620 |
| 8908864 | 12/1989 | Germany . |
| 0109490 | 8/1979 | Japan ................ 73/623 |

Primary Examiner—Hezron E. Williams
Assistant Examiner—Nashmiya Ashraf
Attorney, Agent, or Firm—Jacobson, Price, Holman & Stern

[57] ABSTRACT

An apparatus for inspecting the inner surface (8a) of a hole includes a rotor shaft (12) supported rotatably (14, 16) around its lengthwise axis and movably along the axis and a sensor assembly (7) which is linked by a tilting mechanism (1) with the rotor shaft so that it can be inclined with respect to the axis of the rotor shaft and rotates and moves as the rotor shaft rotates and moves. The sensor assembly selectively assumes the upright position in which its axis coaligns with the lengthwise axis of the rotor shaft, which is necessary for inserting the sensor assembly through a hole (9a) into the hole in the object being inspected, and a titled position in which its axis is inclined with respect to the axis of the rotor shaft, which is necessary for scanning the inner surface (8c) of the hole, by tilting mechanism (1). The rotor shaft is connected to a rotating mechanism (3) and a lifting mechanism (2).

4 Claims, 8 Drawing Sheets

APPARATUS HAVING A PIVOTED EDDY CURRENT PROBE FOR DETECTING FLAWS IN THE INNER SURFACE OF A HOLE

This is a continuation of application Ser. No. 07/841,097, filed Feb. 25, 1992 which is now abandoned.

BACKGROUND OF THE INVENTION

This invention relates to an apparatus for inspecting the inner surface of a hole, and more particularly to an apparatus for inspecting the inner surface of a plug inserted in a heat transfer tube used in a heat exchanger, such as a steam generator, for example.

Figure 9:
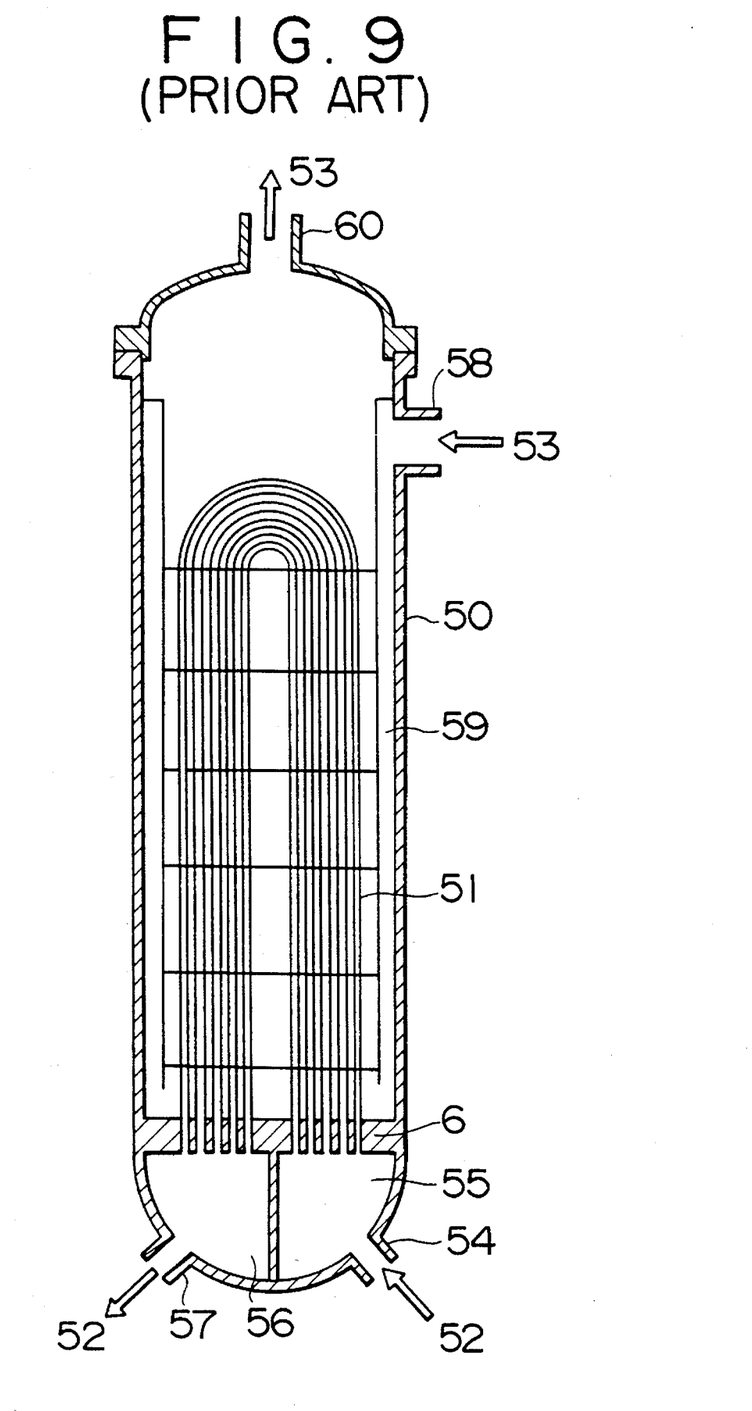
FIG. 9 is a schematic longitudinal cross-sectional view showing a conventional steam generator in which a plug can be inspected by using the inspection apparatus of this invention.

FIG. 9 schematically shows a typical conventional steam generator. The steam generator 50 shown in this figure is a U-shaped tube type, in which heat transfer tubes 51 are formed in a U shape and their ends are secured in a tube plate 6. These heat transfer tubes serve for heat exchange between a primary-side fluid 52 and a secondary-side fluid 53. The primary-side fluid 52 passes through the heat transfer tubes 51 via an inlet nozzle 54 and a high-temperature-side water chamber 55 and flows out of the steam generator 50 via a low-temperature-side water chamber 56 and an outlet nozzle 57. The secondary-side fluid 53, flowing into the steam generator 50 through an inlet nozzle 58, flows down in an annular vertical space 59, and is diverted upwardly over the top surface of the tube plate 6. While the secondary-side fluid 53 rises around and along the outer surface of the heat transfer tubes 51, it is changed into steam by the heat exchange with the primary-side fluid 52 in the heat transfer tube 51, and finally discharged through an outlet nozzle 60.

These heat transfer tubes 51 define a pressure boundary between the primary-side fluid 52 and the secondary-side fluid 53. Therefore, particularly in a nuclear steam generator, they are important elements for preventing the radioactive primary-side fluid 52 from leaking into the usually nonradioactive secondary-side fluid 53. One of the repairing methods to be employed in the event of leakage through the heat transfer tube 51 is one which is generally called a mechanical plugging method.

Figure 10:
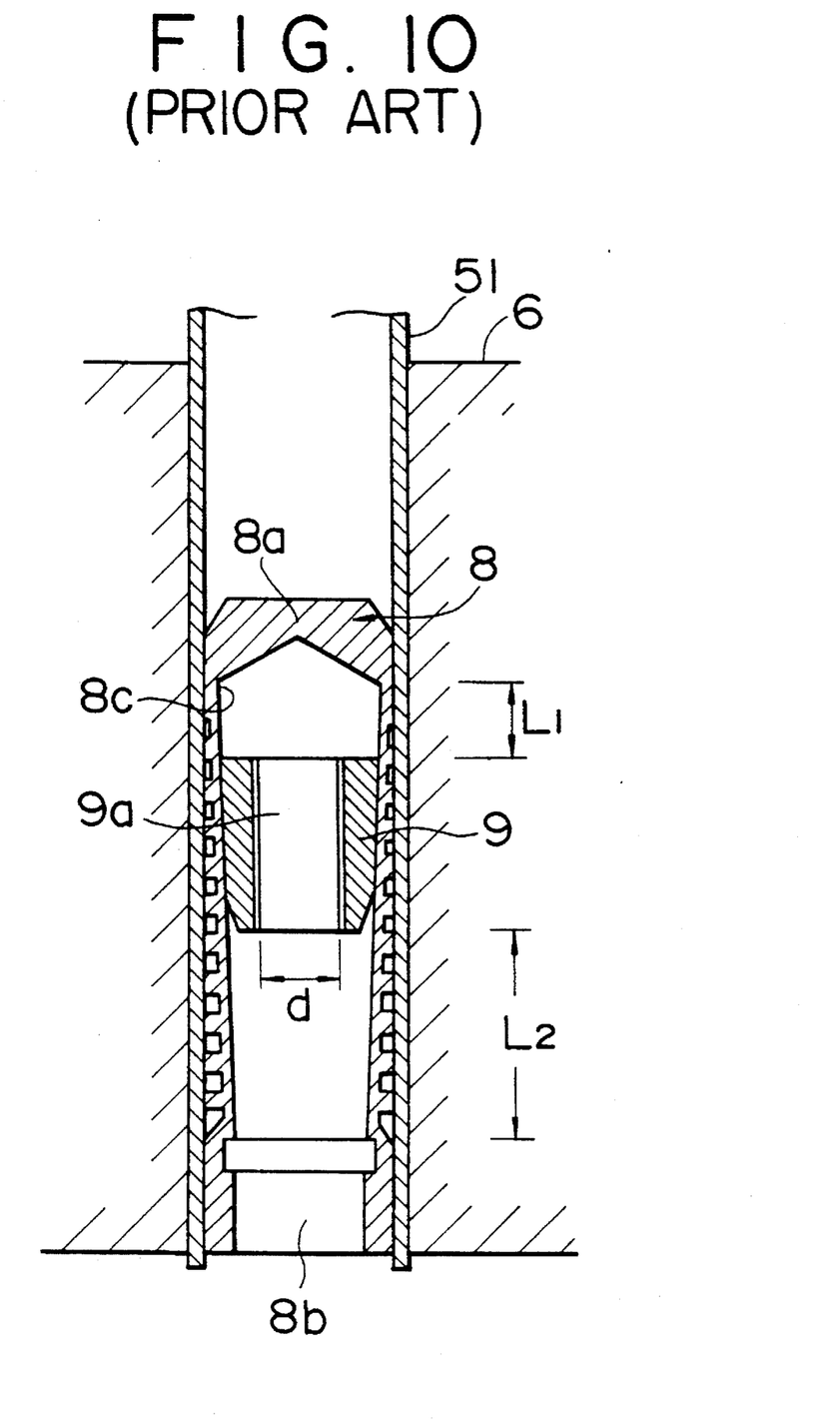
FIG. 10 is a cross-sectional view of an ordinary plug used in a heat transfer tube of conventional steam generator.

FIG. 10 shows a typical conventional plug 8 which can be used for the above-described repair. In this figure, the plug 8 is of a cylindrical shape. This plug 8 has a closed end 8a, while being open at the other end 8b. The inner surface 8c of this plug 8 is in a tapered form such that the inside diameter becomes smaller as it goes from end 8a towards the other end. This plug 8 has a tapered cylindrical member 9 called a wedge core. The wedge core 9 has a through hole 9a in its center, and an internal thread is machined on a surface of the through hole 9a. This wedge core is inserted into the plug before use.

In order to block the heat transfer tube 51 by using the plug 8, the plug 8 is inserted into the inside of the heat transfer tube 51 secured in the tube plate 6 at its both ends, and then the tapered wedge core 9 is pulled down. The internal threads in the through hole 9a are used for threadly engaging a rod or other means for pulling down the wedge core 9.

Thus, the plug 8 is expanded by the wedge action of the wedge core 9, which has been pulled down. By this plug 8, the heat transfer tube 51 is pressed into contact with the wall surface of tube plate 6, and the heat transfer tube 51 is completely blocked, thereby preventing the mixture of the primary-side fluid 52 with the secondary-side fluid 53.

2

In the case where the heat transfer tube 51 leaks, the plug 8 inserted in the above-described manner constitutes a pressure boundary between the primary-side fluid and the secondary-side fluid. Therefore, the plug 8 is also not allowed to have a fluid leak.

So far, however, there has not been provided any suitable tool for detecting any defects in the upper region $L_1$ of the plug above the wedge core and the lower region $L_2$.

The upper region $L_1$ particularly requires timely or scheduled inspections because the upper portion of the plug 8 is exposed to the secondary-side fluid. So far, however, there has been no tool which can insert a sensor (not shown) into the region $L_1$ through the small through hole 9a of diameter d which is used for pulling the wedge core 9 outwardly.

BRIEF SUMMARY OF THE INVENTION

Accordingly, it is an object of this invention to provide an inspection apparatus which can be inserted into a small hole such as defined in a plug for inspection an inner surface of the hole.

To attain the above object, an apparatus for inspecting the inner surface of a hole comprises a rotary shaft supported rotatably around its lengthwise axis and movably along the axis, a sensor assembly which is linked by a tilting mechanism with the rotary shaft so that it can be inclined with respect to the axis of the rotary shaft and can rotate and travel as the rotary shaft rotates and travels, a rotating mechanism which is connected to the rotor shaft and causes the rotary shaft to rotate, and a lifting mechanism which is connected to the rotary shaft so as to cause the rotary shaft to vertically move.

The sensor assembly selectively assumes an upright position in which its axis matches the lengthwise axis of rotary shaft and a tilted position in which the sensor assembly is inclined with respect to the axis of the rotary shaft.

When the inner surface of a hole or a plug is to be inspected, the sensor assembly is inserted into the hole in the upright position, then inclined into a tilted position, so that the sensor portion of the sensor assembly is abutted against the inner surface of the plug. In this condition, the rotor shaft is driven by the rotating mechanism, and the sensor assembly is rotated accompanied with the rotation of the rotor shaft to scan the inner surface. Thus, an inspection over the entire circumference thereof is carried out.

According to the inspection apparatus of this invention, the sensor assembly having the sensor portion can be tilted between an upright position and a tilted position, and also can be raised/lowered and rotated. Therefore, it can be inserted into a small cavity above the wedge core in the plug, and moreover the sensor assembly is inclined into a tilted position after being inserted into the cavity so that its sensor portion comes into contact with or into the opposed position to the inner surface of the hole. Therefore, the entire inner surface of the cavity, which cannot be inspected by the conventional tool, can be scanned by raising/lowering and rotating the sensor assembly. Thus, if the inspection apparatus of this invention is used for the inspection of the plug installed in the heat transfer tube of a nuclear steam generator, valuable data for the maintenance of the heat transfer tubes of the steam generator can be easily obtained.

BRIEF DESCRIPTION OF THE DRAWINGS

The invention will now be described in detail with reference to the accompanying drawings wherein.

DETAILED DESCRIPTION OF PREFERRED EMBODIMENT

The preferred embodiments of this invention will be described hereinafter with reference to the drawings. In the drawings, the same reference numerals indicate the same or corresponding elements. Although the preferred embodiment of this invention is explained for a case in which the inspection of the inner surface of a plug installed in a heat transfer tube of a steam generator is carried out, this invention is not limited to such a case and can be carried out in inspecting the inner surface of a cavity that cannot be inspected by conventional inspection tools.

Figure 1:
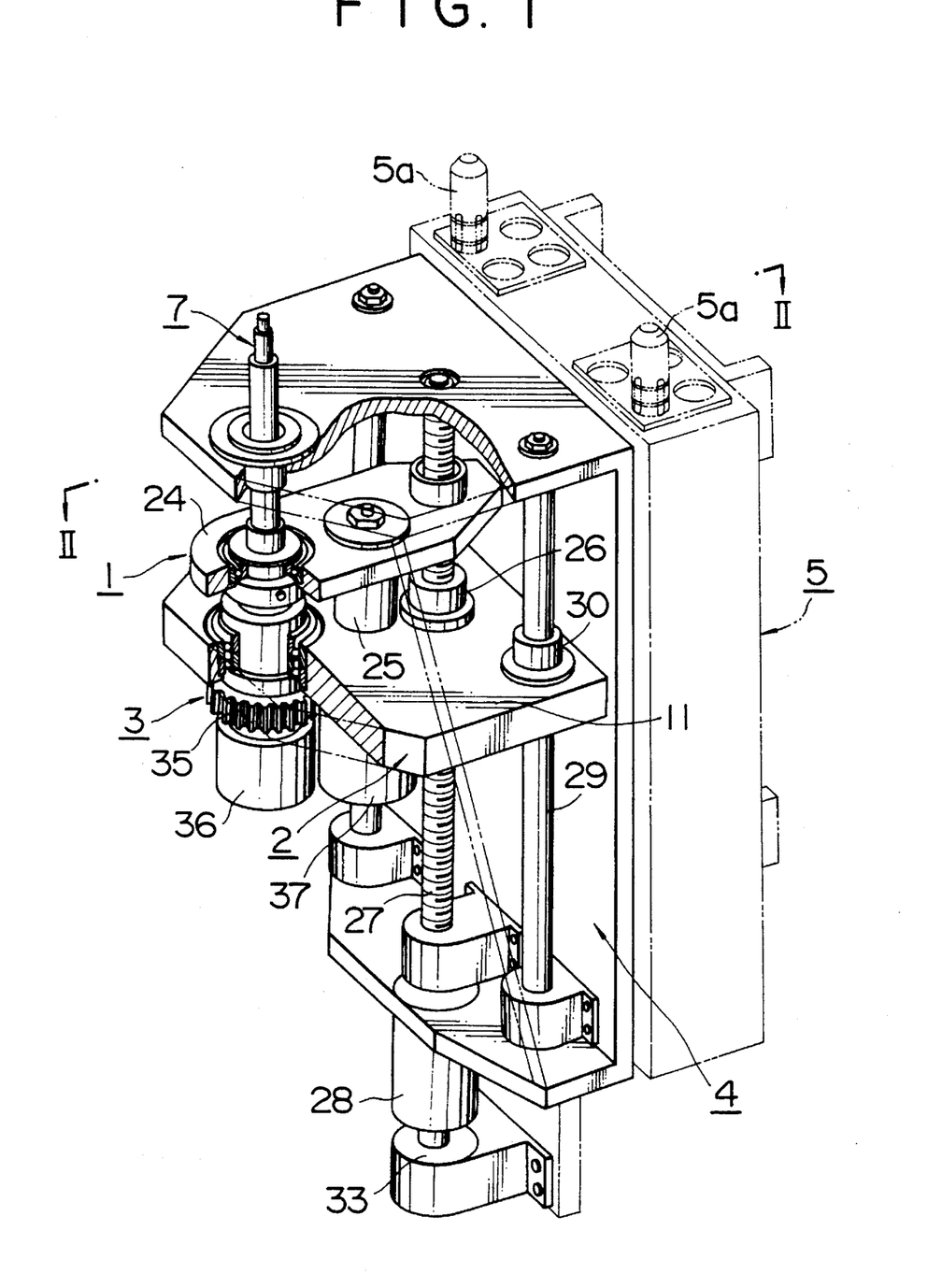
FIG. 1 is a partially cutaway perspective view of an inspection apparatus for inspecting the inner surface of a hole according to this invention.

FIG. 1 schematically shows a general skelton of a plug inspection apparatus of this invention. This plug inspection apparatus includes a tilting mechanism 1, a lifting mechanism 2, a rotating mechanism 3, a casing 4, and a sensor assembly 7. The details of these elements will be described later.

Figure 2:
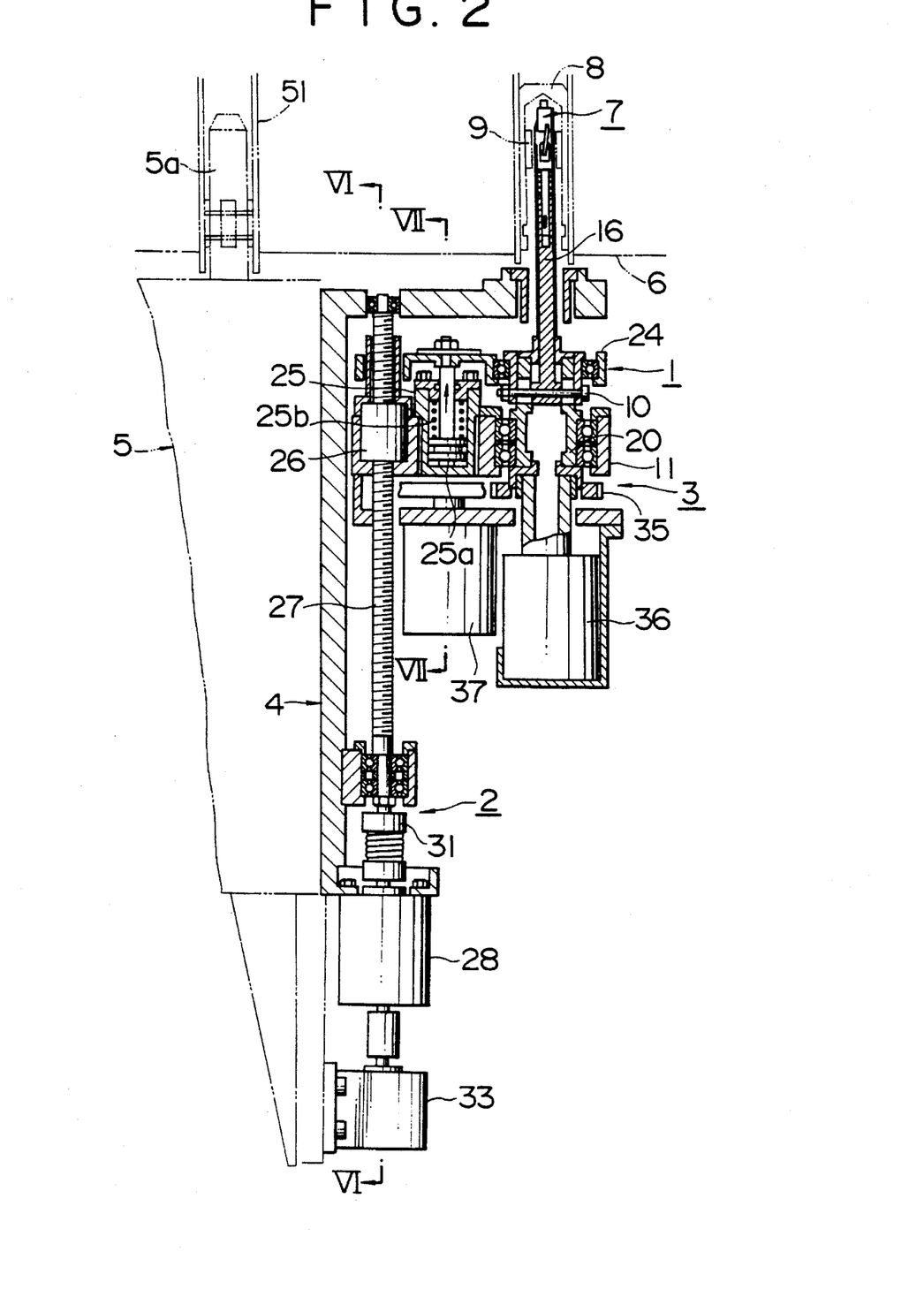
FIG. 2 is a vertical cross-sectional view taken along the plane of the line II—II of FIG. 1.

The plug inspection apparatus can be appropriately set in a specified place where the inspection of the plug 8 to be inspected can be carried out by engaging, in heat transfer tubes near the plug, the protrusions 5a of the clamping means 5 which, in turn, can be of conventional type used in various tools and mounts a casing 4 (refer to FIGS. 1 and 2).

Figure 3:
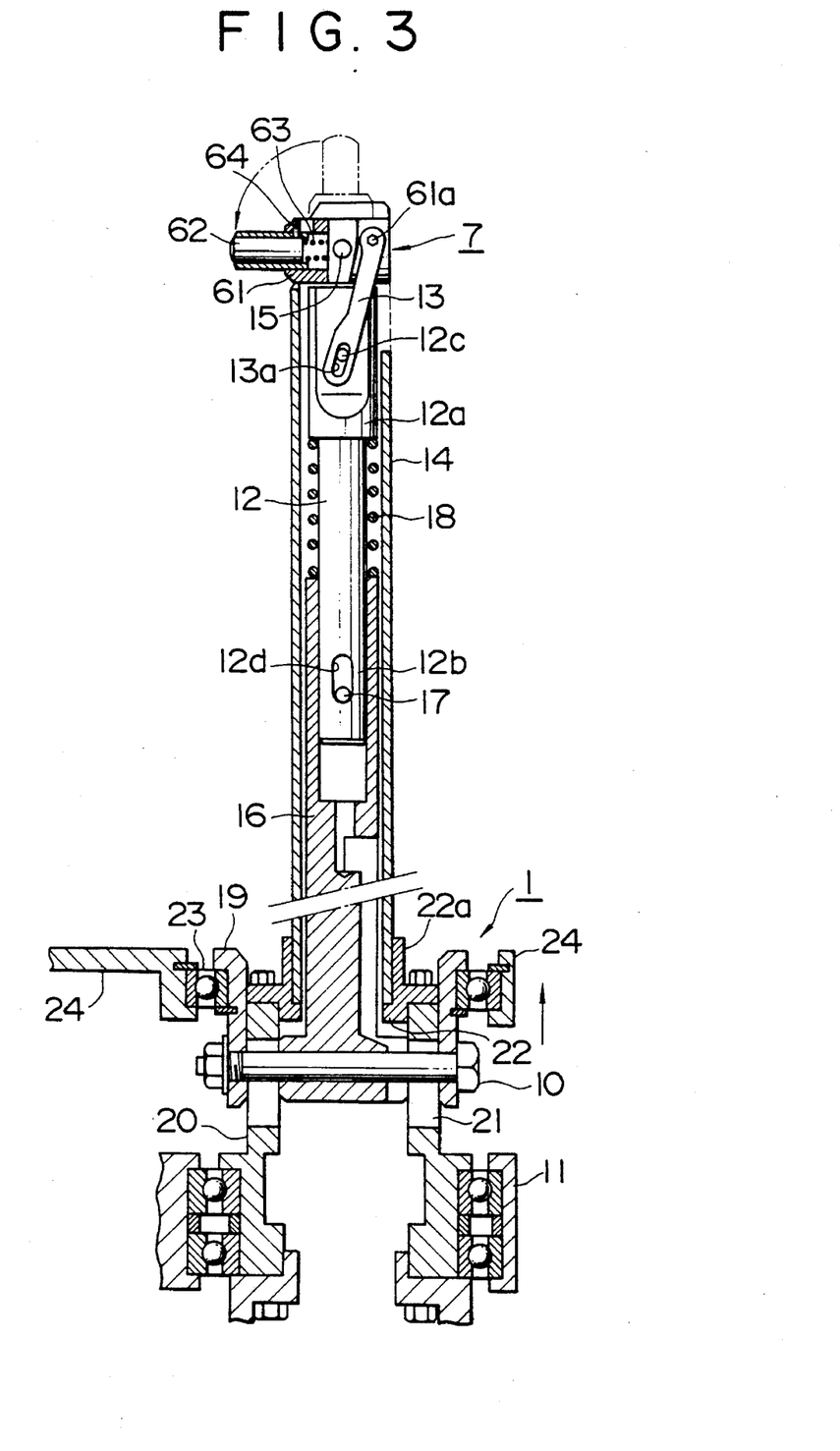
FIG. 3 is a vertical cross-sectional view showing the details of a sensor assembly and a sensor tilting mechanism.

FIG. 2 is a vertical cross-sectional view taken along the plane of the line II—II of FIG. 1. In this figure, the clamping means 5 on which the plug inspection apparatus of this invention is mounted is fixed to a tube plate 6 by engaging the protrusions 5a of the clamping means with the heat transfer tubes 51 as described above. The sensor assembly 7, being held by the tilting mechanism in a way as described later, is illustrated in such a manner that its sensor portion, which will be described later and designated by reference numeral 62 in FIG. 3, is inserted in a wedge core 9 of plug 8 by the lifting mechanism 2. The sensor portion is preferably constituted by a known eddy-current flaw detection sensor, which has been often used for the inspection of inner surfaces of heat transfer tubes.

The tilting mechanism 1 tilts the sensor portion 62 of the sensor assembly 7 through, for example, 90° with respect to the vertical axis from the upright position so that the tip of the sensor portion comes into contact with or into the opposed position to the inner surface of the plug 8. The tilting mechanism 1 is connected to the rotating mechanism 3 by a pin 10. The rotating mechanism 3 is installed on a lift table 11.

Thus, the sensor portion of the sensor assembly 7 is inserted far into the wedge core 9 by lifting the lift table 11 with the lifting mechanism 2. Then, the sensor portion of the sensor assembly 7 is tilted 90° from the upright position to oppose against the inner surface of the plug 8. In addition, the inner surface of plug 8 can be scanned in a circumferential direction by rotating the sensor assembly with the rotating mechanism 3.

Figure 4:
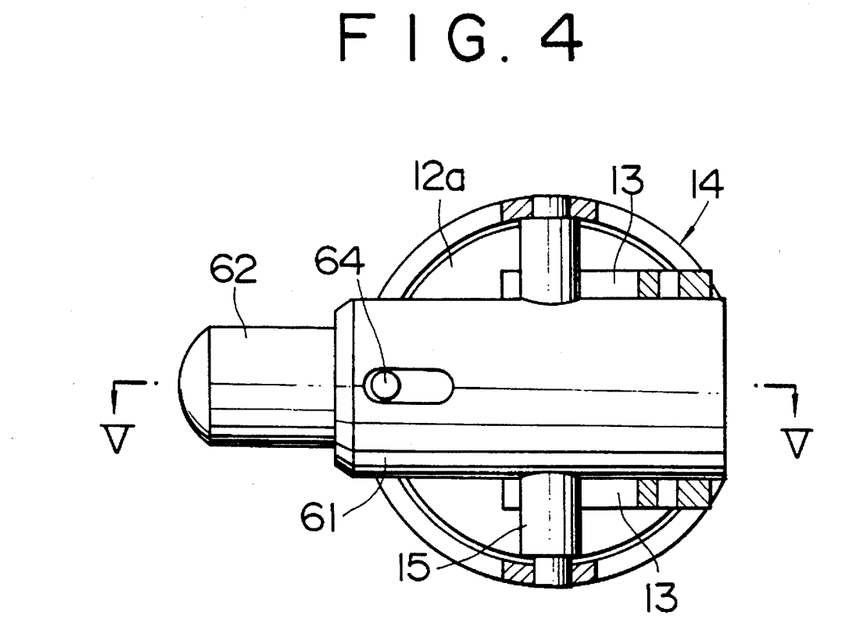
FIG. 4 is an enlarged top plan view of the sensor assembly of FIG. 3.
Figure 5:
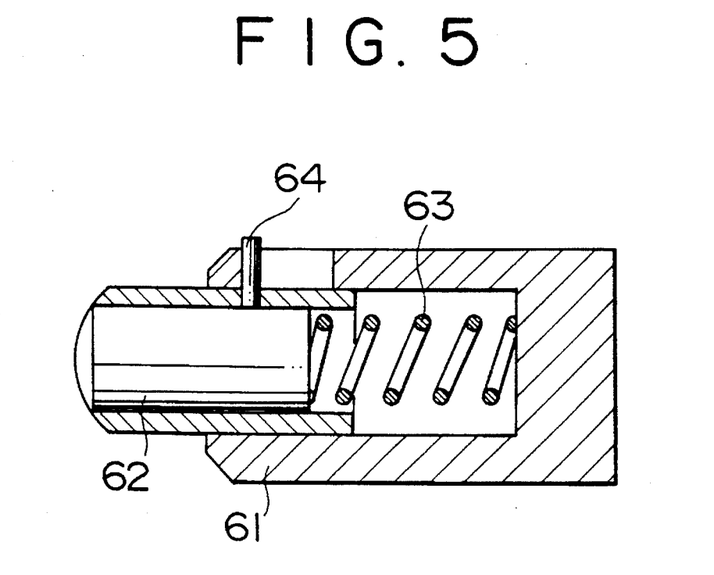
FIG. 5 is a cross-sectional view of the sensor holder taken along the plane of the line V—V of FIG. 4.

FIGS. 3 through 5 show the tilting mechanism 1 and the sensor assembly 7. The sensor assembly 7 comprises a sensor holder 61 which is pivotally mounted to the end of a guide cylinder 14 with a pin 15, a sensor portion 62 held in the sensor holder 61, a coil spring 63 which is received in the sensor holder 61 so as to put the sensor portion 62 onto the inner surface of a plug by being biased in a direction in which the sensor portion 62 protrudes from the sensor holder 61, and a pin 64 extending through a slot 61a in holder 61 for serving as a stopper for the sensor portion 62.

Referring again to FIGS. 3 and 4, to the rear of sensor holder 61 of sensor assembly 7, one end of a link 13 is connected via a pin 61a. The other end of the link 13 is connected to an enlarged diameter portion 12a of a push rod 12 via a joint consisting of a slot 13a and a pin 12c. In the guide cylinder 14, a rotary shaft 16 is housed, and the reduced diameter portion 12b of the push rod 12 is connected to the rotary shaft 16 via a joint consisting of a pin 17 and a slot 12d. A coil spring 18 is mounted between the end of the rotary shaft 16 and the lower shoulder of the enlarged diameter portion 12a of the push rod 12 so as to bias the push rod 12 upward in order to push up the link 13.

The rotary shaft 16 is connected to a traveling cylinder 19 via the pin 10 at its end. The pin 10 extends through a pair of lengthwise slots 21 machined so as to be diametrically opposite each other in a rotating block 20. Therefore, the rotary shaft 16 can not only move along the rotational axis of the rotating block 20 but also rotate together with the rotating block 20.

The lengthwise movement of the rotary shaft 16 causes the tilting operation of the sensor assembly 7 (in this embodiment, a tilt of 90°), and the rotation of the rotor shaft 16 causes the rotation of the sensor assembly 7.

The rotation of the rotary shaft 16 is effected, as described later, by driving a gear 35 mounted under the rotating block 20 (refer to FIG. 2) by a motor 37 shown in FIG. 7. The lower extension of the gear 35 is connected to a slip ring 36 as shown in FIG. 2 so that rotation signals can be picked up.

On the rotating block 20, an ashtray-shaped member 22 is mounted by appropriate fixing means like bolts. The lower end of guide cylinder 14 is firmly fitted to a cylindrical flange 22a of the ashtray-shaped member 22.

In the tilting mechanism 1, the traveling cylinder 19 is supported by a traveling plate 24 via a ball bearing 23. The traveling plate 24 is driven by a piston means 25a shown in FIG. 2 and is moved in the direction indicated by an arrow, so that the sensor assembly 7 is tilted from the upright position as described above.

Figure 6:
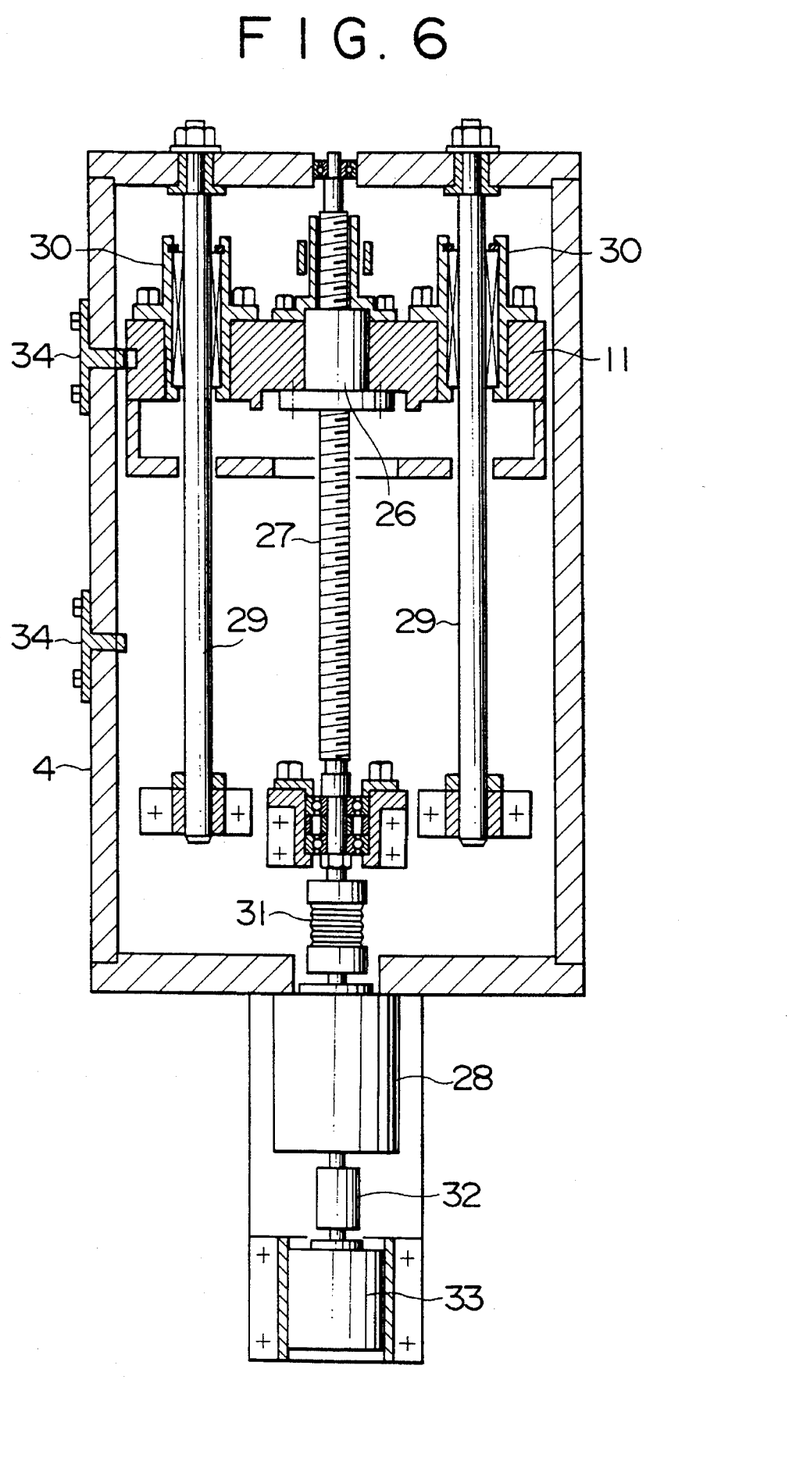
FIG. 6 is an enlarged cross-sectional view of a lifting mechanism in the inspection apparatus of this invention taken along the plane of the line VI—VI of FIG. 2.

FIG. 6 is a cross-sectional view taken along the plane of the line VI—VI of FIG. 2, which is a view for explaining the lifting mechanism 2. On the lift table 11, a ball screw means 26 is mounted. The ball screw shaft 27 of this ball screw mechanism 26 is connected to a motor 28 via a coupling 31. The motor 28 rotates the ball screw shaft 27, by which the lift table 11 can be lifted by the action of two guide shafts 29 and known sliding bearings 30. The output shaft of the motor 28 is connected to not only the ball screw shaft 27 via the coupling 31 but also a rotary encoder 33 via a coupling 32, so that the number of rotations of the output shaft is determined by the rotary encoder, enabling the measurement of the lift distance.

On the casing 4, proximity switches 34 such as Hall elements are disposed spacedly along a lengthwise direction. The signals from the proximity switches 34 are used to control the operation of the motor 28 and restrict the upper and lower limit positions of the lift table 11.

Figure 7:
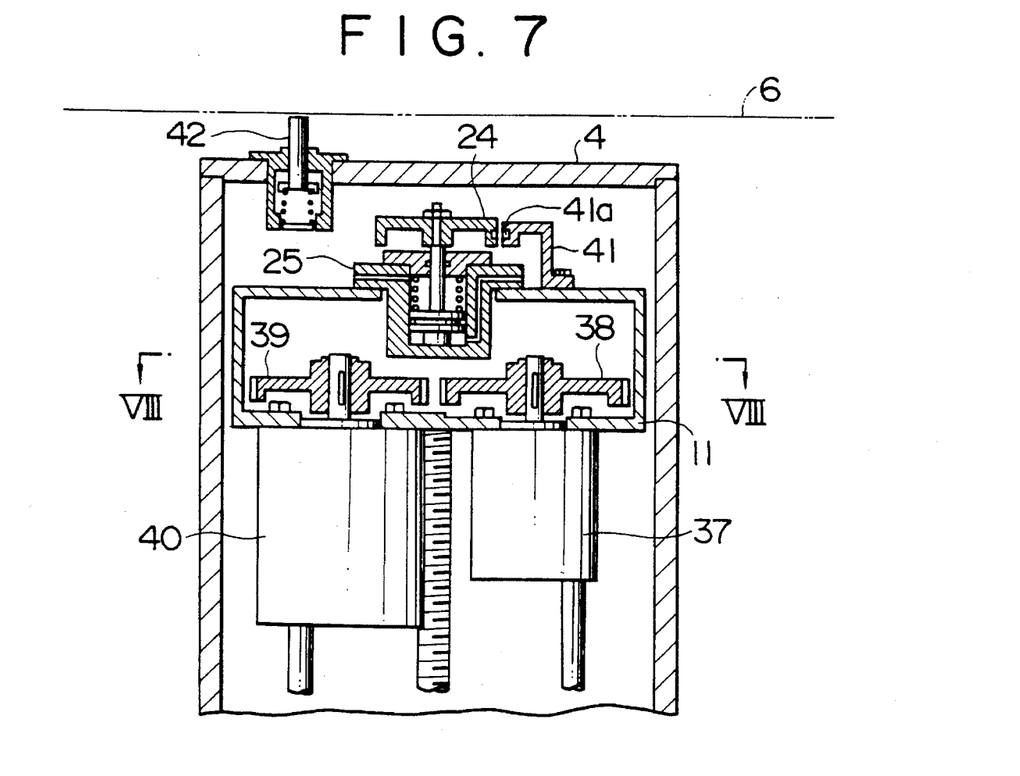
FIG. 7 is an enlarged cross-sectional view of a sensor rotating mechanism in the inspection apparatus of this invention taken along the plane of the line VII—VII of FIG. 2.
Figure 8:
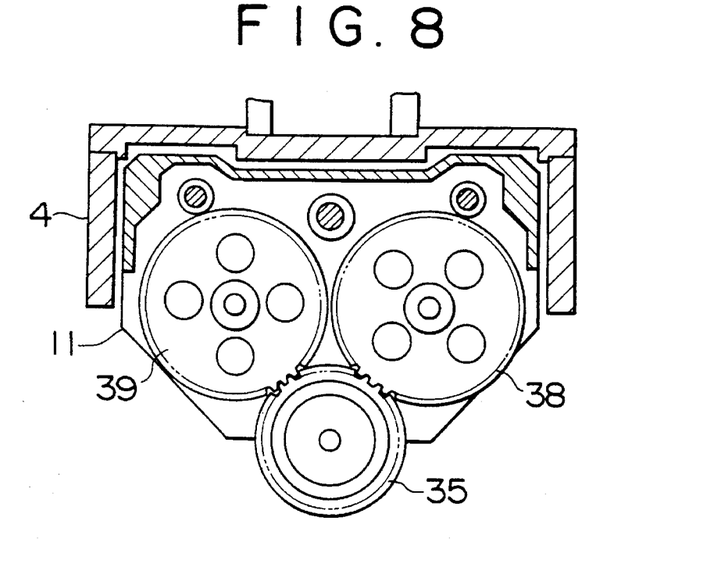
FIG. 8 is a cross-sectional view of the sensor rotating mechanism of FIG. 7 taken along the plane of the line VIII—VIII of FIG. 7.

FIG. 7 is a cross-sectional view taken along the plane of the line VII—VII in FIG. 2, and FIG. 8 is a cross-sectional view taken along the plane of the line VIII—VIII in FIG. 7, each of which shows the details of the sensor rotating mechanism 3. In FIGS. 7 and 8, the motor 37, being fixed to the lift table 11, rotates the above-described gear 35 via a gear 38, and also actuates a rotary encoder 40 via another gear 39 to detect the rotation angle of the sensor assembly 7.

As shown in FIG. 7, a proximity switch 41a such as a Hall element is mounted on the bracket 41 arranged on the lift table 11 in order to monitor the movement of the traveling plate 24 caused by the above-described piston means 25. On the upper surface of the casing 4, a limit switch 42 is mounted. When the plug inspection apparatus reaches a specified position in relation to the tube plate 6, the limit switch 42 generates a signal representing such fact.

The operation of the plug inspection apparatus of this invention in the case where a plug is inspected will be described hereinafter.

When a pressurized fluid is not supplied into the piston means 25, the piston 25a is held at the lowest position by the resilient force of the spring 25b. The sensor assembly 7 is in an upright position indicated by a dash-and-dot line in FIG. 3.

The plug inspection apparatus in this condition is secured in such a manner that the guide cylinder 14 is positioned directly under the heat transfer tube 51 to which a plug 8 is attached, by inserting the protrusions 5a of the clamping means 5 into other heat transfer tubes 51. (Refer to FIG. 2.)

Next, the motor 28 is driven to raise the lift table 11 via the ball screw means 26. When the lift table 11 rises, the rotating block 20 is raised together with the lift table 11, and the guide cylinder 14 is pushed up via the ashtray-shaped member 22. Therefore, the sensor holder 61, which is supported at the upper end of the guide cylinder 14, is also pushed up via the pin 15. When the lift table 11 is raised, the traveling plate 24 is pushed up via the piston means 25, and the rotary shaft 16 is also pushed up as described above, so that the relative position between the rotary shaft 16 and the guide cylinder 14 is unchanged. Therefore, the sensor holder 61 is kept in the upright position as shown in FIG. 2.

Thus, the sensor assembly 7 is inserted into the heat transfer tube 51, and further inserted into the upper space of plug 8 (the portion indicated by $L_1$ in FIG. 10) through the hole 9a in plug 9.

When a pressurized fluid is supplied into the piston means 25, the piston 25a is raised against the force of spring 25b. The rise of piston 25a moves up the traveling plate 24. Together with the traveling plate 24, the traveling cylinder 19 is raised, and the rotary shaft 16 is also raised via the pin 10. When the rotary shaft 16 is raised, the push rod 12 is raised via the pin 17 and the slot 12d. The push rod 12 pushes up the link 13 via the pin 12c and the slot 13a, and the link 13 pushes up the pin 61a of the sensor holder 61. Therefore, the sensor holder 61 is rotated counterclockwise around the pin 15, and placed in the tilted position indicated by a solid line in FIG. 3.

When the motor 37 is driven in this condition, the gear 35 is rotated via the gear 38, and the rotating block 20, which is integral with the gear 35, is rotated. The rotation of the rotating block 20 is transmitted to the traveling cylinder 19 and the rotary shaft 16 via the pin 10. Together with the traveling cylinder 19, the ashtray-shaped member 22, the guide cylinder 14, and the sensor assembly 7 are rotated. Also, together with the rotary shaft 16, the pushing rod 12 is rotated. Therefore, the sensor portion 62 is moved in the circumferential direction on the inner surface 8c of the plug 8.

After the upper portion of plug 8 above the wedge core 9 has been inspected, the motor 28 of the lifting mechanism 2 is driven to lower the lift table 11. When the sensor assembly 7 is lowered by lowering the lift table 11, a part of the sensor holder 61 of the sensor assembly 7 touches the upper edge of the through hole 9a in the wedge core 9. As a result, the spring 18 is compressed and the sensor holder 61 is raised to the upright position, which allows the sensor assembly 7 to pass through the through hole 9a in the wedge core 9. After the sensor assembly 7 has passed through the through hole 9a, the sensor assembly 7 is kept in the tilted position again by the tension of the spring 18, so that the inner surface of plug 8 at the lower portion below the wedge core 9 indicated by $L_2$ in FIG. 10 can be inspected throughout the circumference by using the above-described procedure.

We claim:

1. An apparatus for inspecting an inner cylindrical surface of a hole having an access inlet aperture of smaller diameter than said inner cylindrical surface, comprising:

a casing;

a rotating mechanism mounted on said casing;

a sensor assembly comprising
   a sensor holder having a central axis,
   sensor means comprising at least one eddy-current probe slidably mounted in said sensor holder for reciprocal movement in the direction of said central axis of said sensor holder, and
   spring means between said sensor holder and said sensor means for resiliently urging said sensor means outwardly with respect to said sensor holder;

a tilting mechanism mounted on said rotating mechanism for rotation around a longitudinal axis and comprising
   a guide cylinder having an outer end insertable into said hole to be inspected and an inner end,
   a tilting shaft member reciprocally movable within said guide cylinder in the direction of said longitudinal axis,
   an inner end on said tilting shaft member adjacent said inner end of said guide cylinder,
   an outer end on said tilting shaft member,
   a push rod slidably mounted in said tilting shaft member for sliding movement with respect thereto in the direction of said longitudinal axis, a spring member in said guide cylinder between said shaft member and push rod for resiliently urging said push rod towards said outer end of said guide cylinder, means for pivotally mounting said sensor holder on said outer end of said guide cylinder for tilting said sensor holder between an inserting position wherein said central axis coincides with said longitudinal axis and said sensor holder is partly within said outer end of said guide cylinder, and an inspecting position wherein said central axis extends at an angle with respect to said longitudinal axis, a link member having an inner end pivotally connected to said push rod and an outer end pivotally connected to said sensor holder so that movement of said shaft member in the direction of said longitudinal axis moves said push rod and moves said sensor holder between said inserting position and said inspecting position, a longitudinal slot in said inner end of said link member, a pin member extending from said push rod and slidably engaged in said slot for pivotally connecting said inner end of said link member to said push rod and providing limited substantially longitudinal displacement of said link member relative to said push rod, a slot in said push rod extending in the direction of said longitudinal axis, and a pin member in said tilting shaft member slidably engaged in said slot in said push rod for providing limited longitudinal displacement between said push rod and said tilting shaft member;

said rotating mechanism comprising a hollow rotatable block member rotatably mounted on said casing and having a pair of diametrically oppositely disposed parallel slots therein extending in the direction of said longitudinal axis;

connecting bolt means extending through said pair of slots in said block member and through said inner end of said tilting shaft member to facilitate limited displacement of said tilting shaft member relative to said block member in the direction of said longitudinal axis; and a lifting mechanism connected to said inner end of said guide cylinder and mounted on said casing for reciprocating said rotating mechanism and said tilting mechanism in the direction of said longitudinal axis to insert and retract said sensor assembly through said access inlet aperture into and from said hole.

2. The inspecting apparatus as claimed in claim 1 wherein:

said lifting mechanism comprises reciprocable piston means connected to said rotatable block member so that operation of said piston means by fluid pressure reciprocates said tilting mechanism in the direction of said longitudinal axis.

3. The inspecting apparatus as claimed in claim 1 wherein:

said rotating mechanism further comprises multiple gear means operatively connected to said rotatable block member for rotating said block member upon rotation of said gear means; and means are provided for rotating said gear means.

4. The inspecting apparatus as claimed in claim 2 wherein:

said rotating mechanism further comprises multiple gear means operatively connected to said rotatable block member for rotating said block member upon rotation of said gear means; and means are provided for rotating said gear means.

* * * * *